United States Patent [19]
Hernandez et al.

[11] Patent Number: 5,925,671
[45] Date of Patent: Jul. 20, 1999

[54] ANTITUMOR ISOCOUMARINS

[75] Inventors: Librada Canedo Hernandez, Portal; Cristina Acebal Sarabia, Las Rozas; Dolores Garcia Gravalos, Maldonado, all of Spain

[73] Assignee: Pharma Mar, s.a., Madrid, Spain

[21] Appl. No.: 08/913,099

[22] PCT Filed: Mar. 8, 1996

[86] PCT No.: PCT/GB96/00537

§ 371 Date: Nov. 6, 1997

§ 102(e) Date: Nov. 6, 1997

[87] PCT Pub. No.: WO96/27594

PCT Pub. Date: Sep. 12, 1996

[30] Foreign Application Priority Data

Mar. 8, 1995 [GB] United Kingdom .................. 9504662

[51] Int. Cl.$^6$ .................. A61K 31/35; C07D 311/04; C12P 17/06
[52] U.S. Cl. .................. 514/457; 549/289; 435/125; 435/252.5
[58] Field of Search .................. 514/457; 549/289; 435/125, 252.5

[56] References Cited

U.S. PATENT DOCUMENTS 4,393,225  7/1983  Hayashi .................. 549/289

OTHER PUBLICATIONS

Inouye et al. 'Amicoumacin and SF–2370, Pharmacologically active agents of microbial origin CA 111:208552, 1989.

Itoh et al. 'Chemical structures of Amicoumacins produced by *Bacillus pumilus*, 1983.

*Journal of Medicinal Chemistry*, vol. 26, No.10, 1983, pp.1370–1374.

*The Journal of Antibiotics*, vol. XXXIV, No.5, May, 1981, pp.611–613.

*Agric. Biol. Chem.*, 46(5), 1982, 1255–1259.

*Primary Examiner*—Amelia Owens
*Attorney, Agent, or Firm*—Ernest V. Linek

[57] ABSTRACT

Antitumor isocoumarins are of general formula (III) where R is —$CONH_2$ or —$CH(CH_3)_2$, or a pharmaceutically acceptable addition salt thereof. The compound wherein R is —$CONH_2$ is the known compound amicoumacin A. The compound wherein is —$CH(CH_3)_2$ is a new compound which can be obtained from fermentation of the new marine bacterium *Bacillus sp.* strain M-00-PHD-090, CECT 4546.

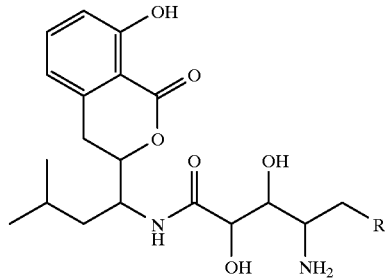

(III)

5 Claims, 5 Drawing Sheets

ANTITUMOR ISOCOUMARINS

FIELD OF THE INVENTION

The present invention relates to isocoumarins having antitumor activity.

BACKGROUND OF THE INVENTION

Amicoumacin A is known from *J. Antibiotics*, 34(5): 611–613, 1981 and from *Agric. Biol. Chem.*, 46(5): 1255–1259, 1982. It has the formula (II):

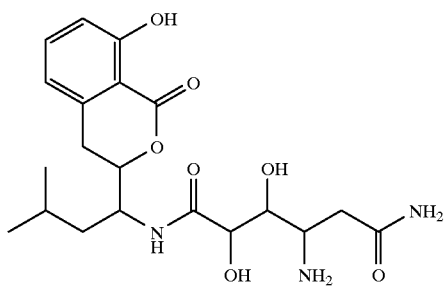

(II)

SUMMARY OF THE INVENTION

We have found antitumour activity in the compound amicoumacin A and in a new compound of related structure. The compounds inhibit protein synthesis.

The present invention provides antitumour isocoumarins of the general formula (III):

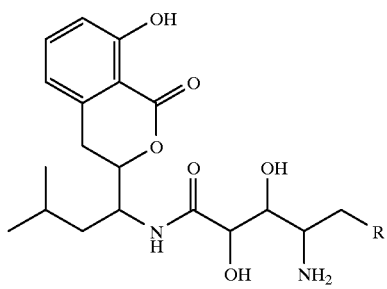

(III)

where R is —CONH; or —C(CH$_3$)$_2$, and pharmaceutically acceptable addition salts thereof.

The compound where R is —CONH$_2$ is amicoumacin A of the formula (II).

The compound where R is —CH(CH$_3$)$_2$ is a new compound is a new designated PM-94128, which was isolated from *Bacillus sp.* CECT 4546 deposited under the Budapest Treaty on Feb. 23, 1995. The compound PM-94128 is of formula (I):

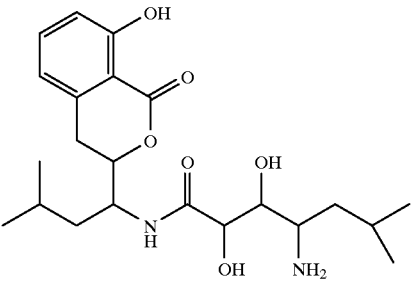

(I)

BRIEF DESCRIPTION OF THE FIGURES

The compound PM-94128 was identified on the basis of detailed analysis of various spectral characteristics. See the data reproduced in FIGS. 1 to 5, wherein.

DETAILED DESCRIPTION OF THE PREFERRED EMBODIMENTS

Figure 1:
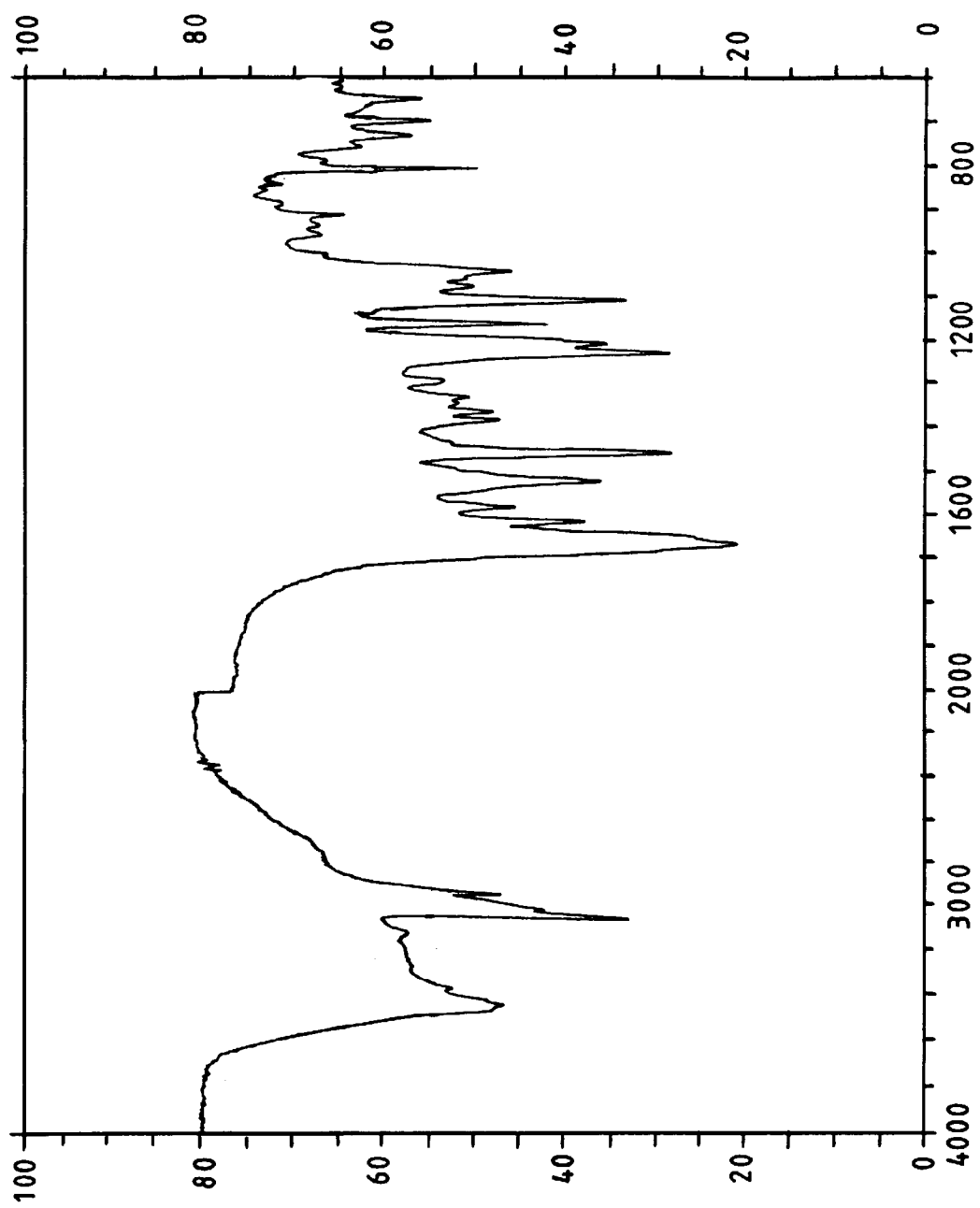
FIG. 1 is the IR absorption spectrum in KBr of PM-94128.
Figure 2:
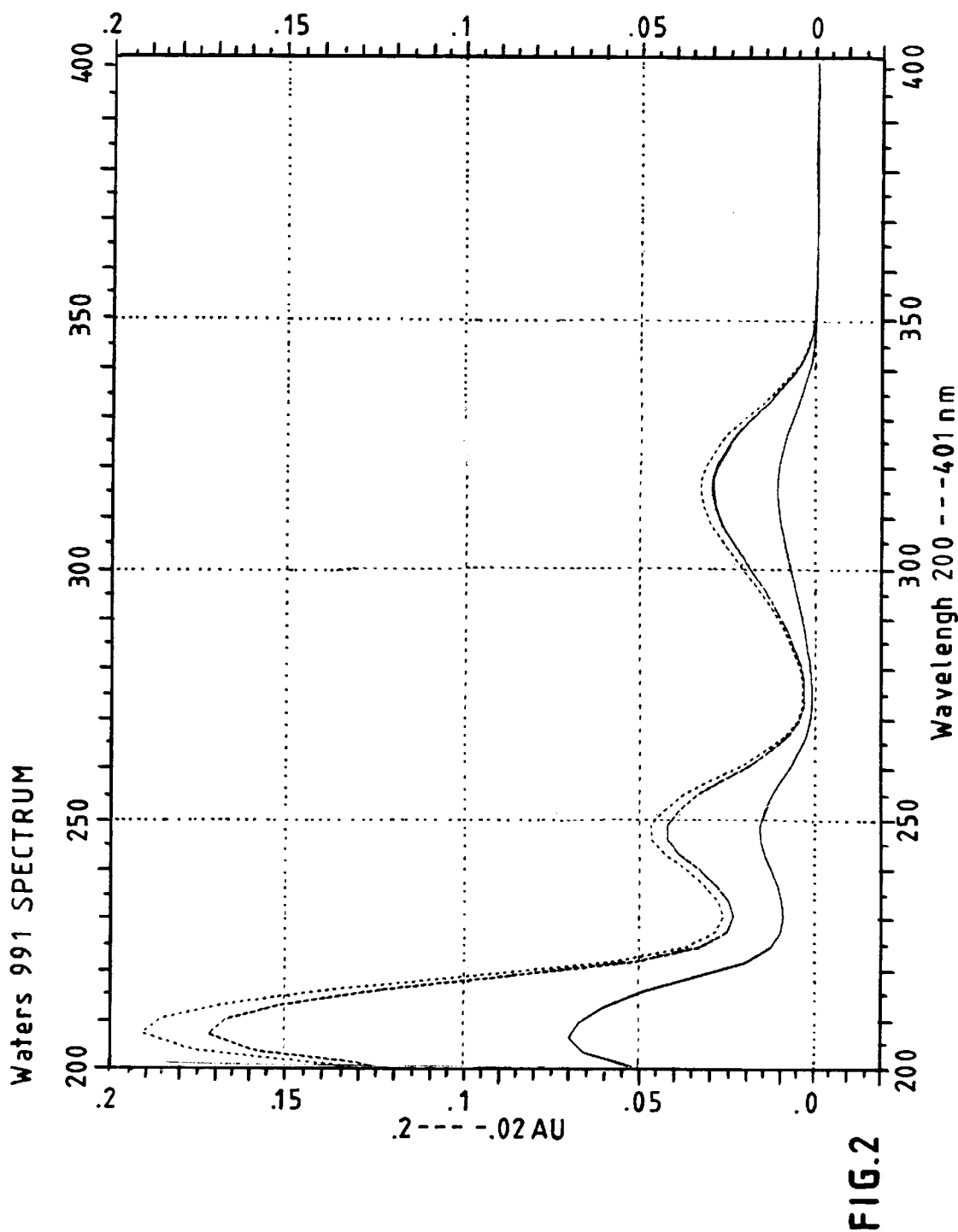
FIG. 2 is the UV spectrum of PM-94128.
Figure 3:
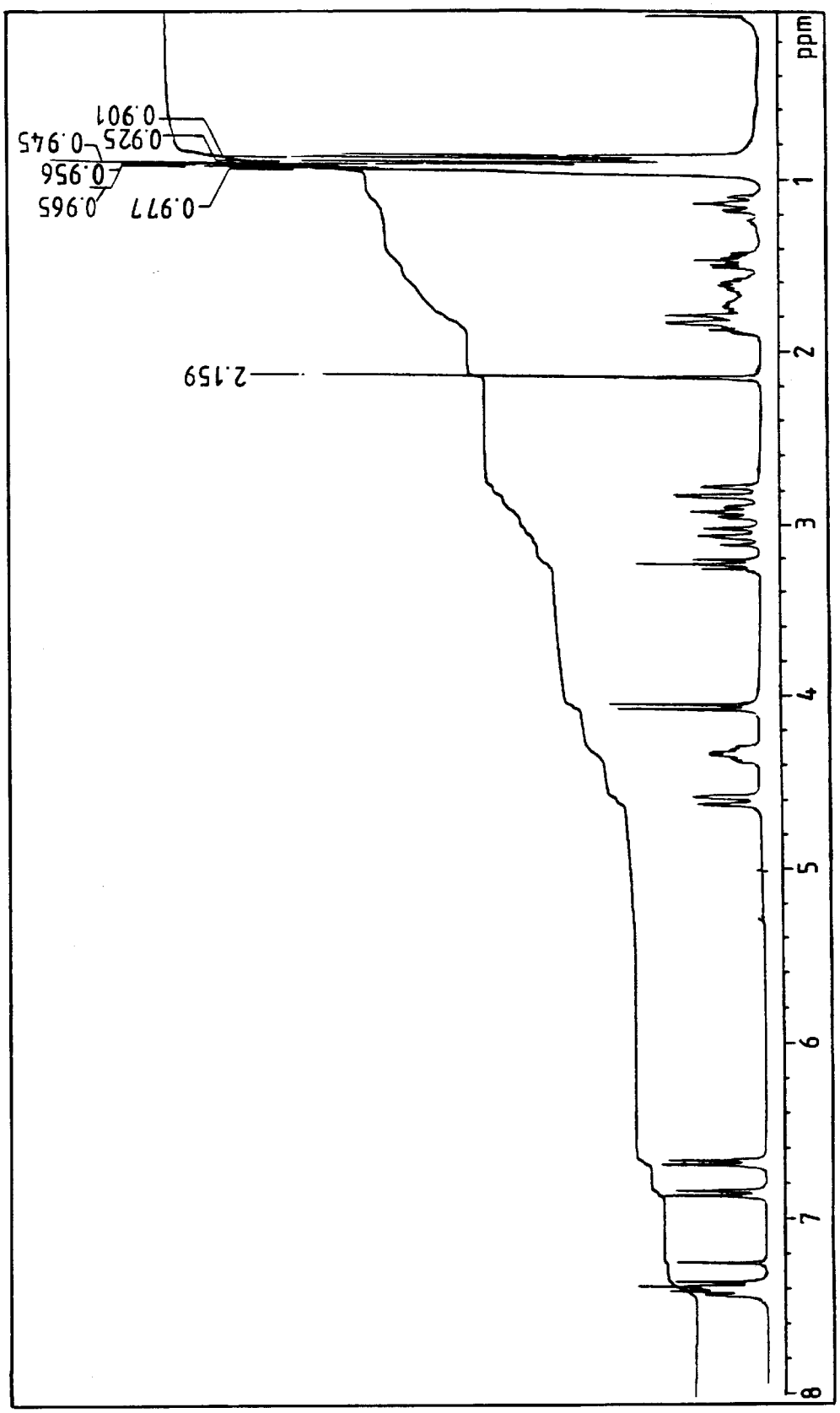
FIG. 3 is the $^1$H NMR of PM-94128.
Figure 4:
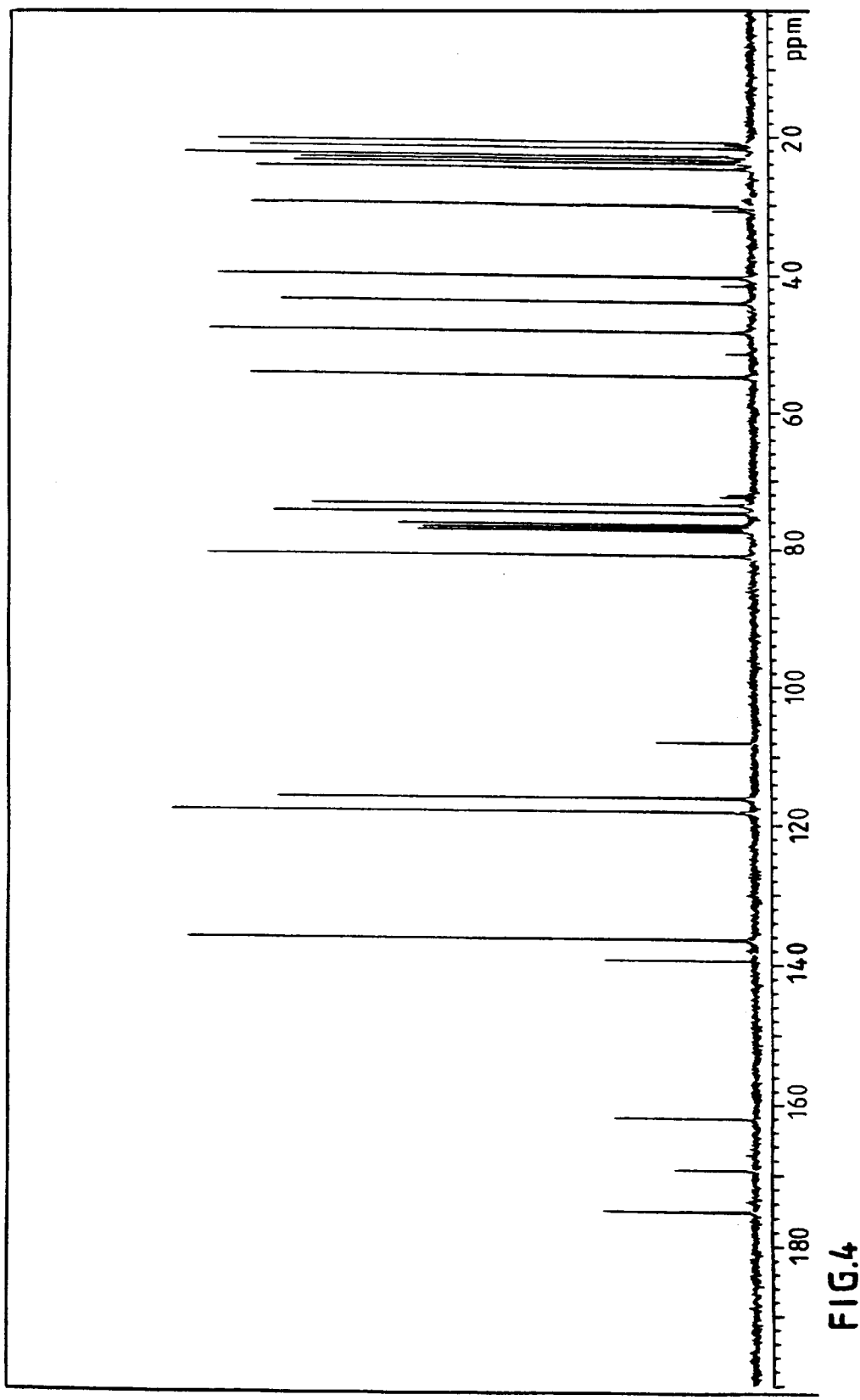
FIG. 4 is the $^{13}$C NMR of PM-94128.
Figure 5:
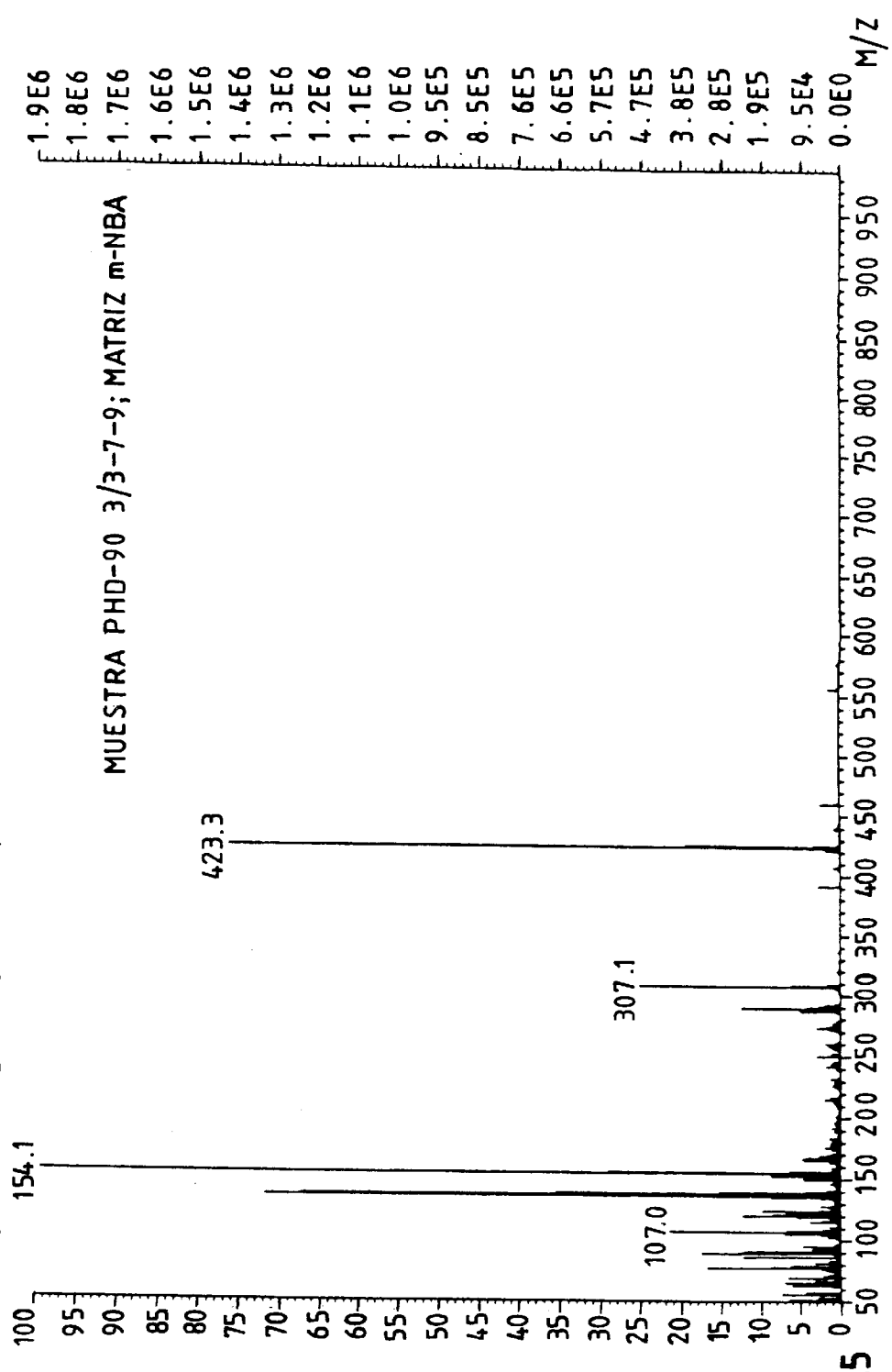
FIG. 5 is the mass spectrum of PM-94128.

The present invention provides antitumor compositions containing the compounds of formula (III) methods of treating tumours using the compounds, processes for preparing the compositions, and a method for preparing the compound of formula (I), among other aspects.

The compounds of the present invention, amicoumacin A and PM-94128, exhibit antitumour activity against cell lines derived from human tumors, such as A-549 human lung carcinoma, HT-29 human colon carcinoma, and MEL-28 human melanoma. They can be employed in a method of treating any mammal affected by malignant tumor sensitive to amicoumacin A or PM-94128, which comprises administering to the affected individual a therapeutically effective amount of the compound or a pharmaceutical composition thereof.

The present invention also relates to pharmaceutical compositions, which contain amicoumacin A or PM-94128 as active ingredient, or a pharmaceutical acceptable acid addition salt thereof.

The pharmaceutical compositions of this invention can be made by admixing the active compound with a pharmaceutically acceptable carrier. Examples of pharmaceutical compositions include any solid (tablets, pills, capsules, granules, etc.) or liquid (solutions, suspensions, or emulsions) with suitable composition of oral, topical or parenteral administration, and they may contain the pure compound or in combination with any carrier or other pharmacologically active compounds. These compounds may need to be sterile when administered parenterally.

The correct dosage of a pharmaceutical composition comprising amicoumacin A or PM-94128 will vary according to the pharmaceutical formulation, the mode of application, and the particular situs, host and bacteria or tumor being treated. Other factors like age, body weight, sex, diet, time of oral administration, rate of excretion, condition of the host, drug combinations, reaction sensitivities and severity of the disease shall be taken into account. Administration can be carried out continuously or periodically within the maximum tolerated dose.

Suitable pharmaceutically acceptable addition salts include salts with inorganic acids such as hydrochloric acid and organic acids such as oxalic or fumaric acid.

The invention also provides a process for obtaining PM-94128, which comprises cultivating a strain of a microorganism capable of producing PM-94128 in aqueous nutrient medium with assimilable carbon and nitrogen sources and salts, under controlled submerged aerobic conditions. The compound PM-94128 can be recovered and purified from the cultured broth.

The preferred microorganism is the *Bacillus sp.* strain designated M-00-PHD-90, which is a new strain of a microorganism capable of producing PM-94128 in an aqueous nutrient medium with assimilable carbon and nitrogen sources and salts, under controlled submerged aerobic conditions. The compound PM-94128 can be recovered and purified from the cultured broth.

*Bacillus sp.* CECT 4546, when cultured under controlled conditions in a suitable nutrient medium produces the compound PM-94128. This strain is preferably grown in an aqueous nutrient medium under aerobic and mesophilic conditions preferably between 24° C. and 35° C. at a pH ranging between 6.0 and 8.0. A wide variety of liquid culture media can be utilized for the cultivation of the microorganism. Useful media are those that include an assimilable carbon source, such as starch, dextrins, glucose, maltose, sugar molasses, and the like, an assimilable nitrogen source such as protein, protein hydrolysate, defatted meals, corn steep, and the like and useful inorganic salts as those found in sea water such as sodium chloride, sulfate, thiosulfate, carbonate, bicarbonate, bromide, etc., and potassium chloride, magnesium sulfate or chloride, etc. Trace elements may be added also. Conventional fermentation tanks have been found to be well suited for carrying out the cultivation of this organism.

ANTITUMOR ACTIVITY

An adapted form of the method described by Bergeron et al ("Antineoplastic an antiherpetic activity of spermidine catecholamide iron chelators" *Biochem. Bioph. Res. Comm.*, 1984, 121(3), 848–854, and see also Schroeder et al, "Effects of Acyclic Pyrimidine Nucleoside Analogues" *Med. Chem.*, 1981, 24 1078–1083) was used to determine the antitumor activity of the compounds of this invention. Three cultures of antitumour cell were employed. A-549 (monolayer culture of a human lung carcinoma, HT-29 (monolayer culture of a human colon carcinoma) and MEL-28 J (monolayer culture of a human melanoma).

A-549, HT-29 and MEL-28 were seeded into 16 mm wells at 2×20" cells per well in 1 ml aliquots of MEM 10FCS containing the identical concentration of drug. A separate set of cultures without drug was seeded a control growth to ensure that cells remained in exponential phase of growth. All determinations were carried out in duplicate. After three days of incubation at 37° C., 10% $CO_2$ in 98% humid atmosphere, the wells were stained with 0.1% Crystal Violet. An approximate $IC_{50}$ was determined by comparing growth in wells with drug to the growth in control wells. The following results were obtained:

| A-549 | HT-29 | MEL-28 |
|---|---|---|
| PM-94128 $IC_{50}$ ($\mu$g/ml) | | |
| 0.02 | 0.02 | 0.02 |
| Amicoumacin A $IC_{50}$ ($\mu$g/ml) | | |
| 0.75 | 1.5 | 0.15 |

MICROORGANISM *Bacillus sp.* M-00-PHD-090 (CETC 4546)

The microorganism was isolated from marine sediment collected in the Pacific Ocean. The taxonomic investigation described herein is based on the following methods:

1. Colonial morphology - Nutrient agar medium (Difco)
2. Cell morphology - Nutrient broth medium (Difco)
3. Oxidase - Kovacs N., Nature, 178: 703 (1956)
4. Biochemical properties - PASCO™ Data Management System (Difco) ID Gram Positive
5. Antibiotic Sensitivity - PASCO™ Data Management System (Difco) MIC Gram Positive All cultures were incubated at 28° C. and records of the results were made after 48 hours incubation time. The descriptions of the culture and test results are as follows:

Colonial morphology: colonies are opaque, low convex, round or irregular, unpigmented.

Cell morphology: singly, straight, motile rods, endospore forming. Spores are oval.

Aerobic: catalase and oxidase are formed.

Biochemical properties: acid is not produced from glucose, arabinose, celloboise, lactose, manose or sucrose. Urease and arginine hydrolase not produced. Phosphatase, $\beta$-glucosidase and $\alpha$-glucopyranoside are produced. Voges-Proskauer is negative.

Antibiotic sensitivity: resistant to bacitracin, teicoplanin and vancomycin. Sensitive to nalidixic acid, novobiocin, ampicillin, penicillin, oxacillin, tretracycline, rifampicin, norfloxacin, erythromycin, cefoxitin, ceflactor, cefuroxime, fosfomicin, streptomycin, gentamicin or amikacin.

Based on the preceding characteristics the culture has been determined to be a species of the genus Bacilus.

The typical steps for the production of PM-94128 by the organism are: Start with either frozen, lyophilized or fresh cells. Obtain the cell mass culturing the initial cells in shake flasks with a culture medium containing some of the ingredients described above at mesophilic temperatures and under aerobic conditions. This step may be repeated several times as needed and the material collected will be used as an inoculum to seed one or several fermentation tanks containing the appropriate culture medium. If desired, these tanks can be used as inoculum or they can serve as the production stage, depending on the broth volume needed.

Typical media that can be used for inoculum development and production of PM-94128 are:

| | Inoculum medium | Production medium |
|---|---|---|
| Tryptone | 5 g | — |
| Yeast extract | 2 g | 2 g |
| Corn steep liquor | — | 4 g |
| Dextrose | 4 g | 10 g |
| $CaCO_2$ | — | 4 g |
| Trace elements solution[1] | — | 1 ml |

-continued

| | Inoculum medium | Production medium |
|---|---|---|
| Instant Ocean Salts[2] | 10 g | 10 g |
| Tap Water | 1000 ml | 1000 ml |

[1] See ATCC medium number 237. American Type Culture Collection Catalog, 1989.
[2] See King and Spote, Marine Ecology, 3: 34 (1976)

It is believed that a wide range of nutrient media may be substituted for those disclosed herein with good growth and production resulting therefrom. Also, it is well known that once a microorganism has been discovered to produce a substance, many other more or less related microorganisms can be isolated with similar production properties.

Antitumor compound PM-94128 can be isolated from the whole fermentation broth by extraction with suitable organic solvent such as ethyl acetate. The extracts from one or two repeated extractions are combined and evaporated to dryness in vacuo.

Separation and purification of PM-94128 from the crude active extract can be performed by the use of the proper combination of conventional techniques, as for example, column chromatography, thin layer chromatography (TLC), medium pressure liquid chromatography, etc.

Fractionation can be guided by antitumoural activity; TLC visualized with UV light at 254 nm and ninhydrin.

EXAMPLE

The present invention will be further illustrated with reference to the following example, which aid in the understanding of the present invention, but which are not to be construed as limitations thereof. All percentages reported herein, unless otherwise specified, are present by weight. All temperatures are expressed in degrees Celsius. All incubations are carried out at 28° C. and flasks are shaken in an orbital shaker at 250 rpm. All media and recipients are sterile and all culture processes aseptic.

Cell Cultures:

Cells were maintained in logarithmic phase of growth in Eagle's Minimum Essential Medium, with Earle's Balanced Salts, with 2.0 mM L-Glutamine, with non-essential Amino Acids, without Sodium Bicarbonate (EMEMNEAA) supplemented with 10% Fetal Calf Serum (FCS), $10^2$ M Sodium Bicarbonate and 0.1 g 1 Penicillin-G-Streptomycin Sulfate.

Stock culture:

Whole broth of a pure culture of Bacillus analogues. M-00-PHD-090 strain (CECT 4546) is preserved frozen in 20% glycerol.

Inoculum:

A well-grown slant culture is used to seed 100 ml of seed medium described previously in a 1000 ml shake flask. This flask is incubated during 48 hrs at 28° C. 500 ml of the same medium in a 2L Erlenmeyer flask are seeded with 5% of the first stage inoculum. The flask is incubated for 24 hrs at 28° C.

Fermentation:

With 500 ml of second stage inoculum seed 10L of production medium already described contained in 15L fermentation tank. The fermentation is carried out during 40 hrs with 250-rpm agitation and air flow of 0.5 WM.V. Monitor secondary metabolite production by assay of whole broth against P-388 cells.

Isolation:

Whole harvest broth (10L) is extracted with 10 L of ethyl acetate. The organic solvent is concentrated and evaporated to dryness in vacuo to yield 2.16 g of crude extract. This extract is dissolved in 300 ml of a mixture NaCl 10% methanol 1:1 and is defatted by partitioning twice with 300 ml of ethylene chloride. The combined organic solvent layer is concentrated in vacuo to give 600 mg of active organic extracts. The extract is chromatographed in silica gel using a mixture of hexane/ethyl acetate as the eluting solvent. The antitumor activity (280 mg) is eluted with hexane/ethyl acetate 75:25. Further purification may be achieved by column chromatography in silica gel and eluted the activity with chloroform/methanol 98.2 (90 mg). The last purification is carried out by column chromatography in C18 reversed phase using water/methanol 15:85 as the eluting solvent to yield 52 mg of pure PM-94128.

What is claimed is:

1. A method of treating mammalian tumors comprising administering to a mammal in need of such treatment, an effective amount of an antitumour composition comprising an isocoumarin of the general formula (III):

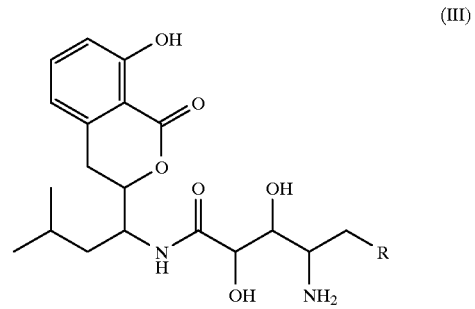

(III)

where R is —$CONH_2$ or —$CH(CH)_2$, or a pharmaceutically acceptable addition salt thereof.

2. An isocoumarin designated PM-94128 of formula (I)

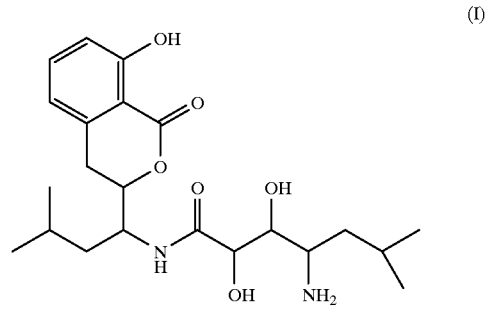

(I)

or a pharmaceutically acceptable salt thereof.

3. A process for obtaining PM-94128, as defined in claim 2, which comprises cultivating a strain of a microorganism capable of producing PM-94128 in an aqueous nutrient medium with assimilable carbon and nitrogen sources and salts, under controlled submerged aerobic conditions.

4. A process according to claim 3, wherein the microorganism is the *Bacillus sp.* strain M-00-PHD-090, CECT 4546.

5. The microorganism *Bacillus sp.* strain M-00-PHD-090, CECT 4546.

* * * * *